United States Patent [19]
Hoyes et al.

[11] Patent Number: 6,030,608
[45] Date of Patent: Feb. 29, 2000

[54] METHOD OF PROCESSING AND PRESERVING ANIMAL URINE AS A LURE

[76] Inventors: David A. Hoyes; Brock A. Hoyes, both of 235 Cameltown Hill Rd., Danville, Pa. 17821

[21] Appl. No.: 09/016,137

[22] Filed: Jan. 30, 1998

[51] Int. Cl.$^7$ ..................................................... A61L 11/00
[52] U.S. Cl. .......................... 424/76.1; 424/76.5; 424/76.6
[58] Field of Search ................................. 424/76.1, 76.5, 424/76.6

[56] References Cited

U.S. PATENT DOCUMENTS 4,437,429  3/1984  Goldstein et al. ........................... 119/1
5,565,111  10/1996  Newman ................................. 210/774

Primary Examiner—S. Mark Clardy
Assistant Examiner—Kathryne E. Shelborne
Attorney, Agent, or Firm—John J. Elnitski, Jr.

[57] ABSTRACT

The present invention is a method and means of enhancing urine based lures by using zeolite to absorb nitrogen and ammonia found in the urine. The method includes several steps of mixing zeolite with urine from the collection stage to the packaging of the urine. The present invention also includes a method and means for enhancing urine based lures that are already packaged and on the shelf for resale.

40 Claims, 2 Drawing Sheets

METHOD OF PROCESSING AND PRESERVING ANIMAL URINE AS A LURE

BACKGROUND

Hunters, photographers and other wildlife enthusiasts attract animals, especially deer, using processed animal urine. The urine naturally has aromatic characteristics or scent which includes pheromones that attract the animal. The urine is processed to remove impurities found in the urine due to the current methods of urine collection. The processed urine is usually from the species of animal which is desired to be attracted. For example, processed deer urine is used by hunters to attract deer during the hunting season of deer. The example of deer urine will be used throughout this specification as it is the predominant animal lure on the market.

The processed deer urine is sold in a bottled liquid form. A major problem with this type of lure is that it has a short shelf life due to degradation of the urine. Mammal urine degrades quickly because it has a high nitrogen content. The high nitrogen content is present because mammals excrete the unused nitrogen from proteins contained in their food through urea. The urea makes up approximately two to five percent (2–5%) of the urine content. After the urine is excreted by mammals, the easily released nitrogen from the urine combines with hydrogen in the urine to form ammonia. The odor from the ammonia masks the pheromones and other scent qualities of the urine which are used to lure the deer, thereby defeating the purpose of the lure. Once the urine is excreted, the production of ammonia begins and as the urine ages, the strength of the ammonia odor increases. Therefore, as the bottled urine sits on the shelf, the nitrogen is continually combining with hydrogen from the urine to form ammonia.

It is an object of the present invention to provide a method and means to reduce and remove the ammonia produced during the processing of animal urine.

It is an object of the present invention to provide a method and means to halt or at least limit the production of ammonia in stored processed urine until it is used for its intended purpose as an animal lure.

It is also an object of the present invention to remove the smell of ammonia from urine based scents that have not been processed according to the present invention.

SUMMARY OF THE INVENTION

The present invention is a method and means of enhancing urine based lures by using zeolite to absorb nitrogen and ammonia found in the urine. The method includes several steps of mixing zeolite with urine from the collection stage to the packaging of the urine. The method includes the step of passing the urine through zeolite to absorb the nitrogen and the ammonia in the urine. Clinoptilolite was one zeolite found to be quite successful for removing the nitrogen and ammonia. In the method, zeolite is also added to collection channels and collection containers so that the absorption process begins at the collection stage of processing the urine. The urine is filtered through the zeolite prior to packaging of the urine. Finally, the urine is packaged with zeolite. Another method disclosed is mixing urine based lures with zeolite which have not been processed with the zeolite to remove the ammonia smell associated with these lures.

DETAILED DESCRIPTION

Figure 1:
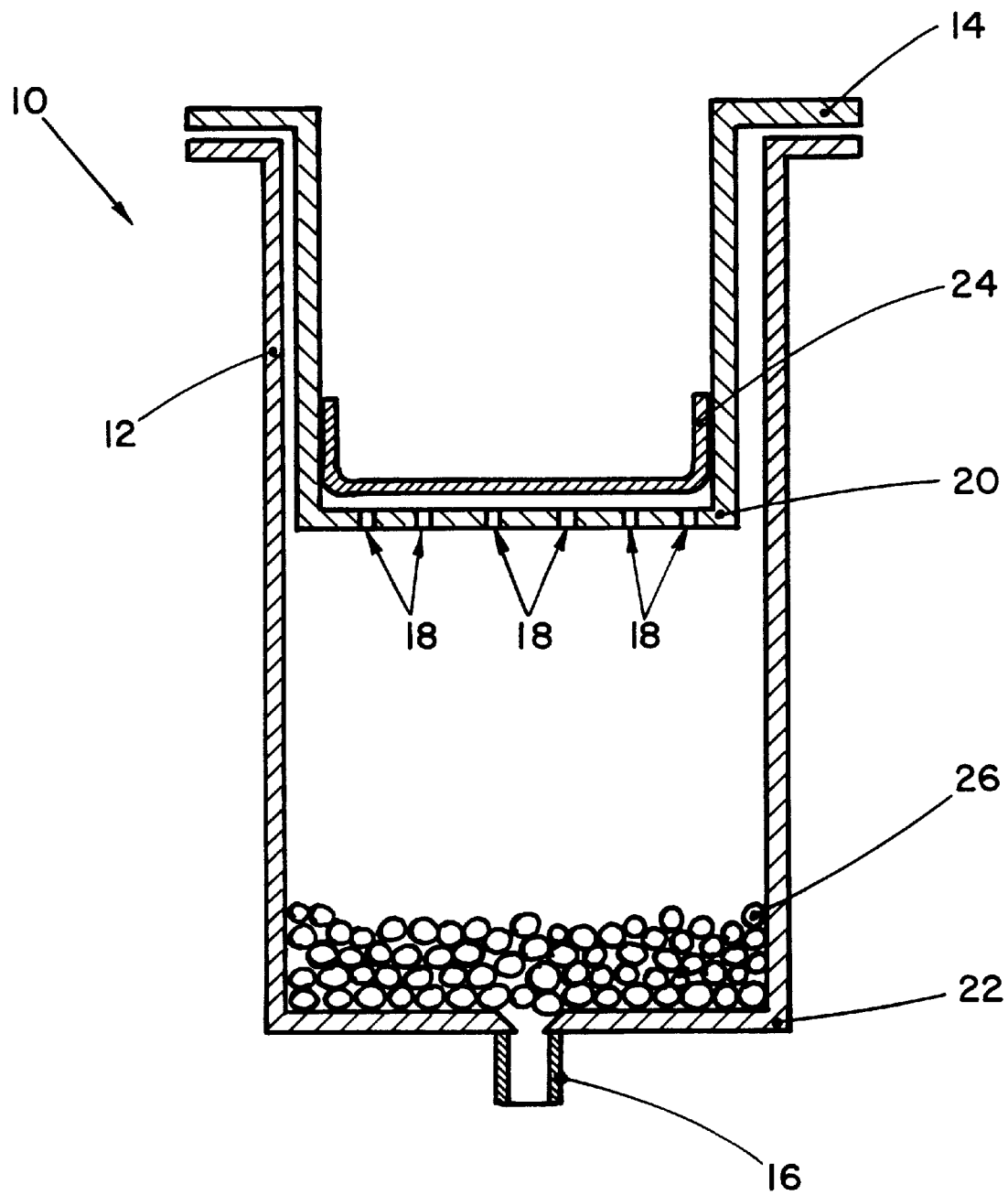
FIG. 1 is a cross-sectional side view of a combination tank according to the present invention.

The typical manner of collecting deer urine is to keep deer in a pen which has a collection system. The collection system is usually a system of grates with openings as part of the pen floor. Under the openings are collection containers or collection channels which lead to collection containers. When the deer excrete the urine, the urine flows through the grate openings into the collection containers, due to gravity. The urine must be processed because the deer also defecate in the pen and the deer feces, as well as other impurities in the pen, mix with the urine. Processing of the urine entails some form of filtering. Filtering removes the unwanted feces and other impurities from the pen that mix with the urine during the collection process. It is immediately upon excretion, during collection and during filtering of the urine when the natural break down of the urine begins and ammonia is produced from the nitrogen and hydrogen in the urine. The method and means of the present invention counteracts this natural break down of the urine, thereby, providing a stronger lure to attract the deer because the scent is not masked by the ammonia.

The present invention is a method and means of using natural or synthetic zeolite during the processing and storage of the deer urine to prevent the formation of ammonia. The zeolite captures or absorbs the nitrogen of the urine. The zeolite can absorb nitrogen oxides, ammonium ions, sulfur dioxide and heavy metals. The zeolite acts as a molecular sieve, matter absorber and catalyst. Clinoptilolite was one particular zeolite found to be particularly successful in the method of the present invention. Clinoptilolite has the chemical name of Potassium-calcium-sodium-aluminosilicate and one of its empirical formulas is $(K_2, Ca, Na_2)O—AL_2O_3—10SiO_2—6H_2O$. Clinoptilolite has a pH stability in the range of 3–10 and can be acquired in the form of various sized stones.

The method begins with placing clinoptilolite stones of various sizes in the collection channels and collection containers. The stones absorb the nitrogen and ammonia in the urine, thereby preventing hydrogen in the urine from combining with the nitrogen. It is believed that hydrogen is an important factor in having a stronger attractant for the deer and should be prevented from combining with the nitrogen. The stone sizes are usually a mixture of fine stones up to approximately one-and-a-half (1½) inch size stones. The urine is removed from the collection channels and collection containers on a daily basis to make room for additional urine collection. The smaller sized stones are used because the larger the stone, the longer it takes to absorb the nitrogen and ammonia. The clinoptilolite is replaced on a regular basis of about every three to seven (3–7) days. When the urine is removed from the collection channels and collection containers, it is filtered through a two step filtering process. The first step is designed to remove solids such as broken down feces and other impurities from the pen. A coffee filter or its equivalent is used in the first step and the first step is repeated if the filter clogs in order to remove all solid impurities. The second step is filtering the urine through a second filter of clinoptilolite. Approximately one-and-a-half to two (1½–2) cubic feet of clinoptilolite are used in the second filtering step. The clinoptilolite is replaced in the second filter after approximately fifty (50) gallons of urine has been filtered.

After the two step filtering process, the urine is ready to be packaged. The urine is usually packaged in an amber colored bottle to protect it from sun light. The urine is bottled depending on how much has been collected. It is preferable to have approximately five (5) gallons at a time before bottling. The bottling in the five gallon quantity allows the control of scent quality. If there is not enough urine to be bottled right away, it is frozen until there is enough available to bottle. The urine can be frozen in a five gallon bucket containing approximately one-and-a-half (1½) cubic feet of clinoptilolite. When the urine is thawed for bottling, it is either placed into a thaw tank with clinoptilolite of variable sizes or thawed in the buckets if it was frozen with the clinoptilolite. The thaw tank has approximately one-and-a-half (1½) cubic feet of clinoptilolite to thaw five (5) gallons of urine at a time. The thawed urine is then drained from the tank for bottling. In order to preserve the urine in the bottle, one (1) oz. of clinoptilolite is placed into a two (2) oz. bottle and one (1) oz. of urine is then added to the bottle. The size of clinoptilolite in the bottles is preferably smaller than bigger to enable the nitrogen and ammonia to be absorbed at a faster rate. The placing of clinoptilolite in the bottle continues the process of absorbing the nitrogen and ammonia from the urine. This provides a lure which utilizes the full potential of the attractive power in the urine and has a longer shelf life.

FIG. 1 illustrates a combination tank 10 to perform the two step filtering process, thawing process and bottling. The combination tank 10 includes a large tank 12, a smaller removable tank 14 and a drain 16. The removable tank 14 rests within the large tank 12 and has a multitude of holes 18 in its bottom 20. The drain 16 is mounted on the bottom 22 of the large tank 12 and is used to drain the processed urine into the bottles (not shown) for sale. With the removable tank 14 installed, a filter 24 is placed in the bottom 20 of the tank 14 to perform the two step filtering process. The filter 24 is usually a coffee filter or its equivalent. The raw urine is placed in the removable tank 14, where it flows into the large tank 12 by way of the filter 24 and the holes 18. There the urine flows through clinoptilolite 26 at the bottom 22 of the large tank 12 and into the drain 16. When the urine is to be thawed, it can be place in the removable tank 14 or placed directly into the large tank 12 if the removable tank 14 has been removed. In either case of thawing, the large tank 12 would have the clinoptilolite 26 at its bottom 22.

Figure 2:
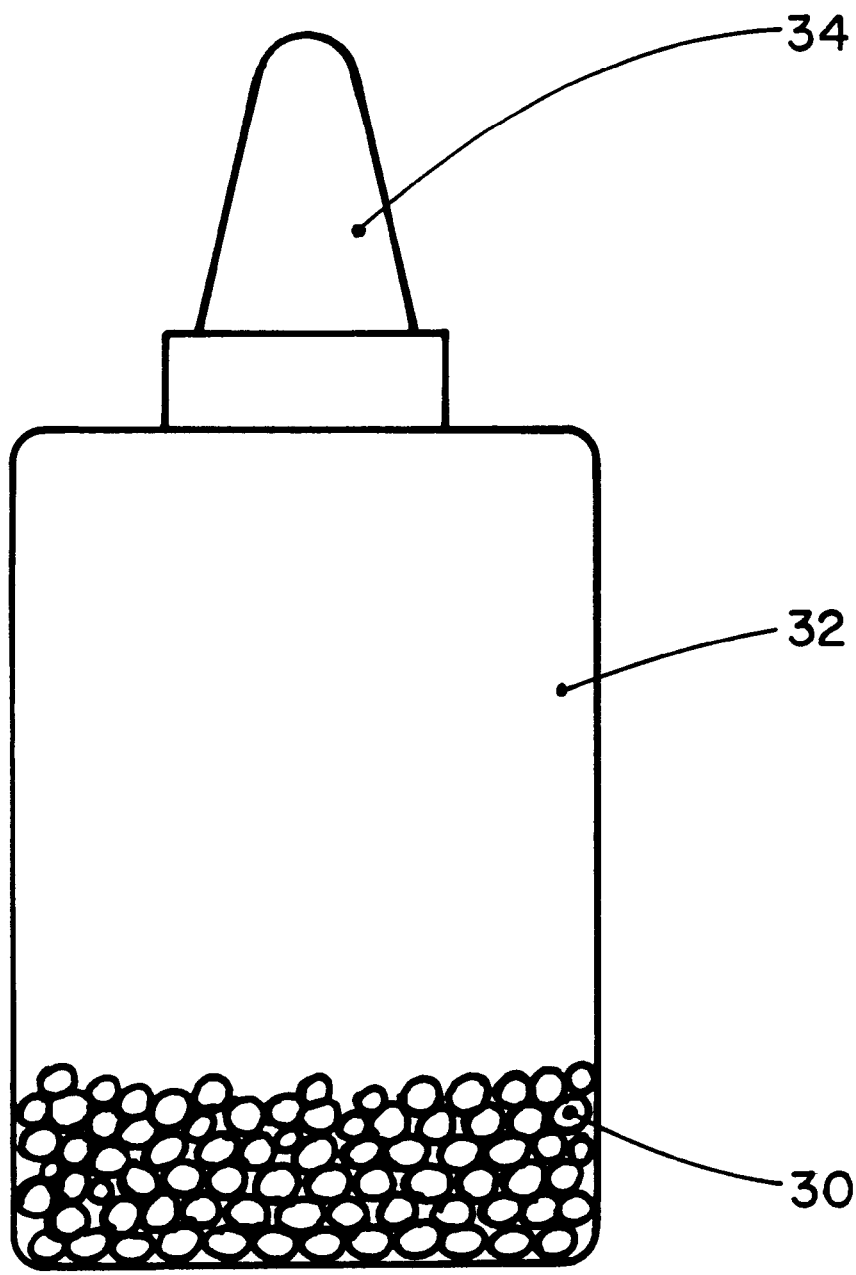
FIG. 2 is an external view of a bottle to mix the urine and zeolite according to the present invention.

At the retail level, many of the urine based scents sold already smell like ammonia when the consumer buys the product. The following is a method and means of enhancing these urine based scents that have an ammonia smell. Packaged clinoptilolite can be provided to add to the urine based scents which have not been processed with clinoptilolite. One method is to provide clinoptilolite that the user can mix with the urine based scent at a ratio of one-to-one (1 to 1). Another method is to provide one (1) oz. of clinoptilolite 30 in a two (2) oz. bottle 32 that includes a squirt cap 34 as shown in FIG. 2. This allows for the user to add the urine based scent that is normally sold in a one (1) oz. container to the clinoptilolite filled bottle. A smaller size stone of the 8 to 14 stones per linear inch are the preferred size in the bottle, as the smaller stones would have a faster rate of removing ammonia.

While embodiments of the invention have been described in detail herein, it will be appreciated by those skilled in the art that various modifications and alternatives to the embodiment could be developed in light of the overall teachings of the disclosure. Accordingly, the particular arrangements are illustrative only and are not limiting as to the scope of the invention which is to be given the full breadth of the appended claims and any and all equivalents thereof.

We claim:

1. A method of enhancing attractive scent qualities of animal urine for attracting animals comprising: filtering the animal urine through zeolite to absorb nitrogen and ammonia in the urine, where the animal urine remains in a liquid state during filtering; and storing said urine that has been filtered for later use to attract said animals.

2. The method of claim 1, wherein the urine is from a mammal.

3. The method of claim 2, wherein the urine is from a deer.

4. The method of claim 1, wherein the zeolite is from a natural source.

5. The method of claim 1, wherein the zeolite is a synthetic zeolite.

6. The method of claim 1, wherein the zeolite is clinoptilolite.

7. A method of collecting and filtering animal urine to enhance attractive scent qualities of the animal urine for attracting animals comprising: providing at least one collection container in a urine collection system which include zeolite to filter the animal urine by absorbing nitrogen and ammonia during collection of the urine into the at least one collection container, where the animal urine remains in a liquid state during filtering; and storing urine that has been filtered for later use to attract said animals.

8. The method of claim 7, further including the step of passing the urine from the at least one collection container through a filter of zeolite prior to packaging the urine.

9. The method of claim 8, further including the step of filtering the urine to remove solid impurities from the urine before packaging.

10. The method of claim 8 further including the step of adding zeolite in the packaging with the urine before the packaging is sealed.

11. The method of claim 7, further including the step of providing zeolite in collection channels which are part of the urine collection system and lead from an initial point of collection to the at least one collection container.

12. A method of preserving urine to prevent masking of scent qualities of the urine for attracting animals comprising: packaging zeolite with the urine to preserve the urine and absorb undesired odors, said urine being in a liquid state and not absorbed by said zeolite when packed with said zeolite; and sealing the packaging of the urine and zeolite for later use of said preserved urine to attract said animals.

13. A scent enhancing system for urine lures comprising zeolite for mixing with said urine lure, said urine lure being in a liquid state; and packaging for mixing said zeolite with said urine lure, said packaging being of a size to allow automatic and proper ratio mixing of said zeolite and urine lure to remove undesired odors which interfere with the attraction of animals.

14. The scent enhancing system of claim 12, wherein said packaging is a squirt bottle.

15. An enhanced urine lure to attract animals produced by the process comprising adding zeolite to urine to produced the enhanced urine lure by absorbing nitrogen and ammonia, where said urine remains in a liquid state; and storing said enhanced urine lure for later use to attract said animals.

16. The enhanced urine lure of claim 15, further including the step of mixing zeolite with the urine during the collection of the urine.

17. The enhanced urine lure of claim 15, further including step of adding zeolite in at least one collection container of a urine collection system.

18. The enhanced urine lure of claim 15, further including the step of filtering urine collected through zeolite.

19. The enhanced urine lure of claim 15, wherein said zeolite is added in the packaging which contains the urine.

20. The enhanced urine lure of claim 15, further including the step of storing urine with zeolite.

21. The enhanced urine lure of claim 15, wherein the zeolite is added to urine after the urine has been processed and packaged for sale.

22. A kit for enhancing a urine lure to attract animals comprising:
   a. zeolite
   b. urine which is of an animal type desired to be attracted;
   whereby said zeolite and urine is combined to enhance said urine's attractive qualities to animals when said zeolite absorbs undesired smells from said urine and said urine remains in a liquid state during the absorption of said undesired smells.

23. The kit of claim 22, further including a measns to mix said zeolite and urine.

24. The kit of claim 22, further including a means for applying said enhanced urine lure.

25. The kit of claim 23, wherein said zeolite is clinoptilolite and said urine is from a deer.

26. The scent enhancing system for urine lures of claim 15, further including packaging which can be sealed for storing said zeolite with said urine lure.

27. The kit of claim 22, wherein said urine is a retail urine based scent sold to attract animals.

28. The method of claim 7, wherein said zeolite is clinoptilolite.

29. The method of claim 8, wherein said zeolite is clinoptilolite.

30. The method of claim 10, wherein said zeolite is clinoptilolite.

31. The method of claim 12, wherein said zeolite is clinoptilolite.

32. The method of claim 13, wherein said zeolite is clinoptilolite.

33. The method of claim 15, wherein said zeolite is clinoptilolite.

34. The method of claim 16, wherein said zeolite is clinoptilolite.

35. The method of claim 17, wherein said zeolite is clinoptilolite.

36. The method of claim 19, wherein said zeolite is clinoptilolite.

37. The method of claim 20, wherein said zeolite is clinoptilolite.

38. The method of claim 21, wherein said zeolite is clinoptilolite.

39. The method of claim 22, wherein said zeolite is clinoptilolite.

40. The method of claim 27, wherein said zeolite is clinoptilolite.

* * * * *